United States Patent [19]

Drabek

[11] Patent Number: 4,734,433

[45] Date of Patent: Mar. 29, 1988

[54] ISOTHIOUREAS AND INSECTICIDAL USE THEREOF

[75] Inventor: Jozef Drabek, Oberwil, Switzerland

[73] Assignee: Ciba-Geigy Corporation, Ardsley, N.Y.

[21] Appl. No.: 934,763

[22] Filed: Nov. 25, 1986

Related U.S. Application Data

[63] Continuation of Ser. No. 676,961, Nov. 30, 1984, abandoned.

[30] Foreign Application Priority Data

Dec. 8, 1983 [CH] Switzerland .................... 6572/83

[51] Int. Cl.[4] .................... C07C 119/20; A01N 37/00
[52] U.S. Cl. ........................................ 514/508; 558/5
[58] Field of Search .............................. 558/5; 514/508

[56] References Cited

FOREIGN PATENT DOCUMENTS 0075205 9/1981 European Pat. Off. ................ 558/5

Primary Examiner—Henry R. Jiles
Assistant Examiner—Robert C. Whittenbaugh
Attorney, Agent, or Firm—Edward McC. Roberts; Meredith C. Findlay

[57] ABSTRACT

The invention relates to novel substituted N-phenyl-N'-acylisothioureas of the formula

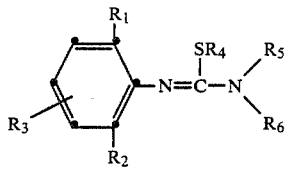

wherein
$R_1$ is $C_1$-$C_5$alkyl,
$R_2$ is hydrogen or $C_1$-$C_5$alkyl,
$R_3$ is hydrogen, halogen, $C_1$-$C_5$alkyl, phenoxy or phenoxy which is substituted by 1 or 2 identical or different members selected from the group consisting of halogen atoms, $C_1$-$C_5$alkyl or trifluoromethyl radicals,
$R_4$ is $C_1$-$C_5$alkyl or propargyl,
$R_5$ is $C_1$-$C_5$alkyl, $C_3$-$C_6$cycloalkyl, allyl or propargyl, and
$R_6$ is a radical selected from —CO—$R_7$, —CO—CO—$R_8$, —SO$_2$—$R_7$ or —CO—O$R_7$, wherein
$R_7$ is $C_1$-$C_5$alkyl, phenyl or phenyl which is substituted by 1 or 2 halogen atoms or methyl groups, and
$R_8$ is $C_1$-$C_{10}$alkoxy or $C_1$-$C_5$dialkylamino.

The invention further relates to the preparation of these compounds and to compositions containing them for use in pest control, in particular for controlling plants and animals which are attacked by insects. The novel compounds are in particular very effect against plant destructive feeding insects.

17 Claims, No Drawings

ISOTHIOUREAS AND INSECTICIDAL USE THEREOF

This is a continuation of application Ser. No. 676,961, filed on Nov. 30, 1984, now abandoned.

The present invention relates to novel substituted N-phenyl-N'-acrylisothioureas, to the preparation thereof, and to the use of these compounds in pest control.

The novel compounds of this invention conform to the formula I

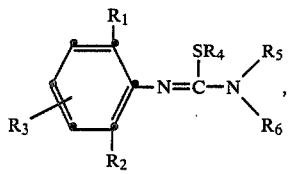

wherein
$R_1$ is $C_1$–$C_5$alkyl,
$R_2$ is hydrogen or $C_1$–$C_5$alkyl,
$R_3$ is hydrogen, halogen, $C_1$–$C_5$alkyl, phenoxy or phenoxy which is substituted by 1 or 2 identical or different members selected from the group consisting of halogen atoms, $C_1$–$C_5$alkyl or trifluoromethyl radicals,
$R_4$ is $C_1$–$C_5$alkyl, allyl or propargyl,
$R_5$ is $C_1$–$C_5$alkyl, $C_3$–$C_6$cycloalkyl, allyl or propargyl, and
$R_6$ is a radical selected from —CO—$R_7$, —CO—CO—$R_8$, —SO$_2$—$R_7$ or —CO—OR$_7$, wherein
$R_7$ is $C_1$–$C_5$alkyl, phenyl or phenyl which is substituted by 1 or 2 halogen atoms or methyl groups, and
$R_8$ is $C_1$–$C_{10}$alkoxy or di($C_1$–$C_5$)alkylamino.

Halogen in the above definition denotes fluorine, chlorine, bromine or iodine, with chlorine being preferred.

Alkyl and alkoxy groups in the definitions of $R_1$ to $R_8$ may be straight chain or branched. Examples of such groups comprise methyl, methoxy, ethyl, propyl, isopropyl, n-butyl, isobutyl, sec-butyl, tert-butyl, n-pentyl, n-hexyl, n-heptyl, n-octyl, n-nonyl, n-decyl and the isomers thereof.

Preferred cycloalkyl groups $R_5$ are cyclopropyl and cyclohexyl.

Preferred compounds of formula I are those wherein
$R_1$ is $C_1$–$C_4$alkyl,
$R_2$ is hydrogen or $C_1$–$C_5$alkyl,
$R_3$ is hydrogen, fluorine, chlorine, $C_1$–$C_3$alkyl, phenoxy or phenoxy which is substituted by 1 or 2 identical or different members selected from the group consisting of fluorine or chlorine atoms, methyl, ethyl or trifluoromethyl groups,
$R_4$ is $C_1$–$C_3$alkyl, allyl or propargyl,
$R_5$ is $C_2$–$C_5$alkyl, $C_3$–$C_6$cycloalkyl, allyl or propargyl, and
$R_6$ is a radical selected from —CO—$R_7$, —CO—CO—$R_8$, —SO$_2$—$R_7$ or —CO—OR$_7$, wherein
$R_7$ is $C_1$–$C_4$alkyl, phenyl or phenyl which is substituted by 1 or 2 identical or different members selected from the group consisting of fluorine or chlorine atoms or methyl groups, and
$R_8$ is $C_1$–$C_4$alkoxy or di($C_1$–$C_3$)alkylamino.

Further preferred compounds of formula I are those wherein
$R_1$ is $C_1$–$C_4$alkyl,
$R_2$ is $C_1$–$C_5$alkyl,
$R_3$ is hydrogen, fluorine, chlorine, methyl, phenoxy or phenoxy which is substituted by a member selected from the group consisting of fluorine, chlorine, methyl or trifluoromethyl,
$R_4$ is $C_1$–$C_3$alkyl, allyl or propargyl,
$R_5$ is $C_2$–$C_5$alkyl, cyclopropyl, cyclohexyl, allyl or propargyl, and
$R_6$ is a radical selected from —CO—$R_7$ or —CO—CO—$R_8$, wherein
$R_7$ is methyl, ethyl, phenyl or phenyl which is substituted by a fluorine or chlorine atom, and
$R_8$ is methoxy, ethoxy or dialkylamino in which alkyl is methyl or ethyl.

On account of their biological, in particular insecticidal, properties, preferred compounds of formula I are those wherein
$R_1$ is $C_1$–$C_3$alkyl,
$R_2$ is $C_2$–$C_5$alkyl,
$R_3$ is hydrogen or 4-phenoxy,
$R_4$ is $C_1$–$C_3$alkyl, allyl or propargyl,
$R_5$ is $C_2$–$C_5$alkyl,
$R_6$ is a radical selected from —CO—$R_7$ or —CO—CO—$R_8$, wherein
$R_7$ is methyl, ethyl, phenyl or difluorophenyl, and
$R_8$ is methoxy, ethoxy, dimethylamino or diethylamino; in particular those compounds of formula I wherein
$R_1$ is $C_1$–$C_3$alkyl,
$R_2$ is $C_2$–$C_4$alkyl,
$R_3$ is hydrogen or 4-phenoxy,
$R_4$ is methyl,
$R_5$ is $C_1$–$C_4$alkyl, and
$R_6$ is a —CO—CH$_3$ or —CO—CO—OC$_2$H$_5$ radical.

The compounds of formula I are prepared by procedures analogous to known ones (cf. for example U.S. Pat. No. 4 357 351) by reacting an isothiourea of formula II

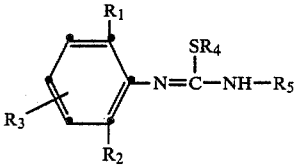

with a halide of formula III $$X—R_6 \qquad (III)$$

in which formulae II and III above $R_1$ to $R_8$ are as defined for formula I and X is a halogen atom, preferably a chlorine atom.

The process for the preparation of the compounds of formula I is conveniently carried out in the temperature range from −30° to +100° C., preferably from 0° to 50° C., under normal or slightly elevated pressure, and ordinarily in the presence of a solvent or diluent which is inert to the reactants. Particularly suitable are non-polar and aprotic solvents or diluents, e.g. ethers and ethereal compounds such as diethyl ether, diisopropyl ether, dioxan and tetrahydrofuran.; aromatic hydrocarbons such as benzene, toluene and xylenes; ketones such as acetone, methyl ethyl ketone and cyclohexanone; as well as acetonitrile, dimethylsulfoxide and dimethylformamide.

The above reaction is normally carried out in the presence of a base to give a free compound of formula I. If a base is not used, then the corresponding salts, i.e. hydrohalides, are obtained. Such hydrohalides can be converted into salts of the desired kind by known methods, optionally with other acids. Suitable bases are inorganic bases such as KOH, NaOH, NH$_4$OH or alkali metal carbonates, e.g. NaHCO$_3$, and organic bases such as trialkylamines, e.g. triethylamine or ethyl diisopropylamine, pyridine, dialkylanilines and others.

Some of the starting compound of formulae II and III employed in the above process are known. Those that are novel can be readily prepared from known precursors by conventional procedures.

Thus the isothioureas of formula II can be obtained by S-alkylation of appropriate ureas with alkyl, allyl or propargyl halides (q.v. U.S. Pat. No. 4 404 225, European patent specification No. 0 025 010 and DE-OS No. 27 30 620).

Insecticidal N-phenoxyphenyl-N'-alkylisothioureas are described in U.S. Pat. No. 4 328 247. It is further known from U.S. Pat. No. 4 357 351 that N-phenyl-N'-acylisothioureas which do not carry a reactive hydrogen atom at the N'-nitrogen atom have insecticidal properties with reduced phytotoxic side effects. In contradistinction thereto, the compounds of this invention are novel and have pronounced insecticidal activity, in particular against harmful pests in rice.

In particular, the compound of formula I are suitable for controlling insects of the orders Lepidoptera, Coleoptera, Homoptera, Heteroptera, Diptera, Thysanoptera, Anoplura, Siphonaptera, Mallophaga, Thysanura, Isoptera, Psocoptera and Hymenoptera.

The compounds of formula I are also suitable for controlling representatives of the order Acarina of the families: Ioxididae, Argasidae, Tetranychidae and Dermanyssidae. They can also be used with success for controlling in particular phytopathogenic mites, e.g. of the families Tetranychidae and Phytoptipalpidae (spider mites), Tarsonemidae (soft-bodied mites) and Eriophidae (gall mites).

In addition to their activity against mosquitoes and flies, e.g. *Aëdes aegypti* and *Musca domestica* as well as aphids, the compounds of formula I can also be used for controlling plant destructive insects in ornamentals and crops of useful plants, especially in cotton crops (e.g. against *Spodoptera littoralis* and *Heliothis virescens*), and in crops of cereals, fruit and vegetables (e.g. against *Laspeyresia pomonella*, *Leptinotarsa decemlineata* and *Epilachna varivestis*). The compounds of formula I are also very effective against larval insect stages and nymphs, in particular of harmful feeding insects. The compounds of this invention are also suitable for controlling soil insects (e.g. *Aulacophora femoralis*, *Chortophila brassicae*, *Diabrotica balteata*, *Pachnada savignyi* and *Scotia ypsilon*).

In particular, the compounds of formula I can be very successfully used against plant destructive cicadas, especially in rice crops, against which pests they exhibit both systemic and contact action.

The compounds of formula I can further be used for controlling ectoparasitic insects and acaridnae on domestic animals and productive livestock, for example by treating animals, cowsheds, barns, stables etc., and pastures.

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, chlorinated hydrocarbons, and *Bacillus thuringiensis* preparations. Compounds of formula I can be combined with particular advantage with diazinone, dioxacarb, heptenophos and isoprocarb to obtain effective insecticidal compositions which are especially suitable for controlling harmful insects in rice crops.

The compounds of the formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tall oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atom in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or lower hydroxyalkyl radicals. The salts are preferably in the form of halides, methylsulfates or ethylsulfates, e.g. stearyltrimethylammonium chloride or benzyldi-(2-chloroethyl)-ethylammonium bromide.

The surfactants customarily employed in the art of formulation are described e.g. in "McCutcheon's Detergents and emulsifiers Annual", MC Publishing Corp. Ridgewood, N.J., 1979, and Dr. Helmut Stache "Tensid Taschenbuch", Carl Hanser Verlag, München/Wien 1981.

The pesticidal compositions usually contain 0.1 to 99%, preferably 0.1 to 95%, of a compound of the formula I or a combination thereof with other insecticide or acaricides,, 1 to 99.9% of a solid or liquid adjuvant, and 0 to 25%, preferably 0.1 to 20%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

Formulation Examples for liquid active ingredients of the formula I or combinations thereof with other insecticides or acaricides (throughout, percentages are by weight)

| 1. Emulsifiable concentrates | (a) | (b) | (c) |
|---|---|---|---|
| active ingredient or active ingredient combination | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |
| xylene mixture | 65% | 25% | 20% |

Emulsions of any required concentration can be produced from such concentrates by dilution with water.

| 2. Solutions | (a) | (b) | (c) | (d) |
|---|---|---|---|---|
| active ingredient or active ingredient combination | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| expoxidised coconut oil | — | — | 1% | 5% |
| ligroin (boiling range 160–190°) | — | — | 94% | — |

These solutions are suitable for application in the form of microdrops.

| 3. Granulates | (a) | (b) |
|---|---|---|
| active ingredient or active ingredient combination | 5% | 10% |
| kaolin | 94% | — |
| highly dispersed silicic acid | 1% | — |
| attapulgite | — | 90% |

The active ingredient or active ingredient combination is dissolved in methylene chloride, the solution is sprayed onto the carrier, and the solvent is subsequently evaporated off in vacuo.

| 4. Dusts | (a) | (b) |
|---|---|---|
| active ingredient or active ingredient combination | 2% | 5% |
| highly dispersed silicic acid | 1% | 5% |
| talcum | 97% | — |
| kaolin | — | 90% |

Ready for use dusts are obtained by intimately mixing the carriers with the active ingredient or active ingredient combination.

Formulation Examples for solid active ingredients of the formula I or combinations thereof with other insectidies or acaricides (throughout, percentages are by weight)

| 5. Wettable powders | (a) | (b) | (c) |
|---|---|---|---|
| active ingredient or active ingredient combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or active ingredient combination is thoroughly mixed with the adjuvants and the mixture is thoroughly ground in a suitable mill, affording wettable powders which can be diluted with water to give suspensions of any desired concentration.

| 6. Emulsifiable concentrate | |
|---|---|
| active ingredient or active ingredient combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 7. Dusts | (a) | (b) |
|---|---|---|
| active ingredient or active ingredient combination | 5% | 8% |
| talcum | 95% | — |
| kaolin | — | 92% |

Ready for use dusts are obtained by mixing the active ingredient or active ingredient combination with the carriers, and grinding the mixture in a suitable mill.

| 8. Extruder granulate | |
|---|---|
| active ingredient or active ingredient combination | 10% |
| sodium lignosulfonate | 2% |
| carboxymethylcellulose | 1% |
| kaolin | 87% |

The active ingredient or active ingredient combination is mixed and ground with the adjuvants, and the mixture is subsequently moistened with water. The mixture is extruded and then dried in a stream of air.

| 9. Coated granulate | |
|---|---|
| active ingredient or active ingredient combination | 3% |
| polyethylene glycol 200 | 3% |
| kaolin | 94% |

The finely ground active ingredient or active ingredient combination is uniformly applied, in a mixer, to the kaolin moistened with polyethylene glycol. Non-dusty coated granulates are obtained in this manner.

| 10. Suspension concentrate | |
|---|---|
| active ingredient or active ingredient combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or active ingredient combination is intimately mixed with the adjuvants, giving a suspension concentrate from which suspensions of any desired concentration can be obtained by dilution with water.

EXAMPLE 1

Preparation of N-(4-phenoxy-2,6-diisopropylphenyl)-N'-tert-butyl-N'-carbethoxycarbonyl-S-methylisothiourea

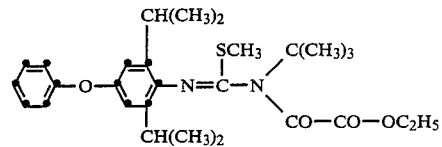

9.9 g of N-(4-phenoxy-2,6-diisopropylphenyl)-N'-tert-butyl-S-methylisothiourea are dissolved in 50 ml of methylene chloride. 3.32 ml of triethylamine and then, at 5°–10° C., 3.0 g of ethyl oxalate chloride are added dropwise to this solution. The reaction mixture is stirred for 3 hours at room temperature and then washed with water. The separated organic phase is dried over $Na_2SO_4$ and the solvent is distilled off. The crude residue is chromatographed through a column of silica gel and eluted with a 1:1 mixture of hexane/ether, affording the title compound as a viscous oil with $n_D^{20}$: 1.5470 (compound 1).

The following compounds of formula I are prepared in analogous manner:

| Compound No. | $R_1$ | $R_2$ | $R_3$ | $R_4$ | $R_5$ | $R_6$ | Physical data |
|---|---|---|---|---|---|---|---|
| 2 | —CH(CH$_3$)$_2$ | —CH(CH$_3$)$_2$ | H | —CH$_3$ | —CH(CH$_3$)$_2$ | —CO—CO—OC$_2$H$_5$ | $n_D^{20}$ = 1.5350 |
| 3 | —CH(CH$_3$)$_2$ | —CH(CH$_3$)$_2$ | 4-O-C$_6$H$_5$ | —CH$_3$ | —C(CH$_3$)$_3$ | —CO—CH$_3$ | m.p. 91–93° C. |

-continued

| Compound No. | $R_1$ | $R_2$ | $R_3$ | $R_4$ | $R_5$ | $R_6$ | Physical data |
|---|---|---|---|---|---|---|---|
| 4 | $-C_2H_5$ | $-CH(C_2H_5)-CH_3$ | H | $-CH_3$ | $-CH(CH_3)_2$ | $-CO-CO-OC_2H_5$ | $n_D^{20} = 1.5352$ |
| 5 | $-C_2H_5$ | $-CH(C_2H_5)-CH_3$ | H | $-CH_3$ | $-CH(CH_3)_2$ | $-CO-CH_3$ | $n_D^{20} = 1.5469$ |
| 6 | $-C_2H_5$ | $-CH(C_2H_5)-CH_3$ | H | $-CH_3$ | $-C(CH_3)_3$ | $-CO-CO-OC_2H_5$ | $n_D^{20} = 1.5372$ |
| 7 | $-C_2H_5$ | $-CH(C_2H_5)-CH_3$ | H | $-CH_3$ | $-C(CH_3)_3$ | $-CO-CH_3$ | $n_D^{20} = 1.5471$ |
| 8 | $-C_2H_5$ | $-CH(CH_3)_2$ | H | $-CH_3$ | $-CH(CH_3)_2$ | $-CO-CH_3$ | $n_D^{20} = 1.5509$ |
| 9 | $-C_2H_5$ | $-CH(CH_3)_2$ | H | $-CH_3$ | $-CH(CH_3)_2$ | $-CO-CO-OC_2H_5$ | $n_D^{20} = 1.5398$ |
| 10 | $-CH_3$ | $-CH(CH_3)_2$ | H | $-CH_3$ | $-CH(CH_3)_2$ | $-CO-CO-OC_2H_5$ | $n_D^{20} = 1.5420$ |
| 11 | $-CH_3$ | $-CH=CH_3)_2$ | H | $-CH_3$ | $-CH(CH_3)_2$ | $-CO-CH_3$ | $n_D^{20} = 1.5550$ |
| 12 | $-CH(CH_3)_2$ | $-CH(CH_3)_2$ | H | $-CH_3$ | $-n-C_4H_9$ | $-CO-CH_3$ | $n_D^{20} = 1.5371$ |
| 13 | $-CH_3$ | $-CH(CH_3)_2$ | H | $-CH_3$ | $-C(CH_3)_3$ | $-CO-CH_3$ | $n_D^{20} = 1.5478$ |
| 14 | $-CH(CH_3)_2$ | $-CH(CH_3)_2$ | H | $-CH_3$ | $-n-C_4H_9$ | $-CO-CO-OC_2H_5$ | $n_D^{20} = 1.5295$ |
| 15 | $-CH(CH_3)_2$ | $-CH(CH_3)_2$ | H | $-CH_3$ | $-CH_3$ | $-CO-CO-OC_2H_5$ | $n_D^{20} = 1.5426$ |
| 16 | $-CH(CH_3)_2$ | $-CH(CH_3)_2$ | H | $-CH_3$ | $-CH_3$ | $-CO-CH_3$ | m.p. 84–86° C. |
| 17 | $-C_2H_5$ | $-CH(CH_3)_2$ | H | $-CH_3$ | $-C(CH_3)_3$ | $-CO-CH_3$ | $n_D^{20} = 1.5502$ |
| 18 | $-CH(CH_3)_2$ | $-CH(CH_3)_2$ | H | $-CH_3$ | $-C(CH_3)_3$ | $-CO-CO-OC_2H_5$ | $n_D^{20} = 1.5820$ |
| 19 | $-CH(CH_3)_2$ | $-CH(CH_3)_2$ | H | $-CH_3$ | $-CH(CH_3)_2$ | $-CO-CO-OCH_3$ | m.p. ca. 70° C. |
| 20 | $-CH(CH_3)_2$ | $-CH(CH_3)_2$ | H | $-CH_3$ | furyl (2-furyl) | $CO-CO-OC_2H_5$ | $n_D^{21} = 1.5384$ |
| 21 | $-CH(CH_3)_2$ | $-CH(CH_3)_2$ | H | $-CH_3$ | $-CH(CH_3)_2$ | $-CO-CH_3$ | $n_D^{21} = 1.5451$ |
| 22 | $-C_2H_5$ | $-CH(C_2H_5)-CH_3$ | 4-O-phenyl | $-CH_3$ | $-CH(CH_3)_2$ | $-CO-CH_3$ | $n_D^{21} = 1.5694$ |
| 23 | $-CH(CH_3)_2$ | $-CH(CH_3)_2$ | H | $-CH_3$ | $-C(CH_3)_3$ | $-CO-CO-OCH_3$ | $n_D^{21} = 1.5327$ |
| 24 | $-CH(CH_3)_2$ | $-CH(CH_3)_2$ | H | $-C_2H_5$ | $-CH(CH_3)_2$ | $-CO-CO-OC_2H_5$ | $n_D^{21} = 1.5208$ |
| 25 | $-CH(CH_3)_2$ | $-CH(CH_3)_2$ | H | $-CH_3$ | $-CH(CH_3)_2$ | $-CO-CO-OC_4H_9(i)$ | $n_D^{21} = 1.5248$ |
| 26 | $-CH_3$ | $-CH_3$ | H | $-CH_3$ | $-CH(C_2H_5)-CH_3$ | $-CO-CO-OCH_3$ | $n_D^{21} = 1.5499$ |
| 27 | $-CH_3$ | $-CH_3$ | H | $-CH_3$ | $-C(CH_3)_3$ | $-CO-CO-OCH_3$ | m.p. 62–70° C. |
| 28 | $-CH(CH_3)_2$ | $-CH(CH_3)_2$ | 4-O-phenyl | $-CH_3$ | $-CH(CH_3)_2$ | $-CO-CO-OC_4H_9(i)$ | $n_D^{23} = 1.5449$ |

-continued

| Compound No. | R₁ | R₂ | R₃ | R₄ | R₅ | R₆ | Physical data |
|---|---|---|---|---|---|---|---|
| 29 | $-CH(CH_3)_2$ | $-CH(CH_3)_2$ | 4-O-C₆H₄- | $-CH_3$ | $-CH(CH_3)_2$ | $-CO-CH_2-CH(CH_3)_2$ | $n_D^{23}=1.5498$ |
| 30 | $-CH(CH_3)_2$ | $-CH(CH_3)_2$ | 4-Br | $-CH_3$ | $-CH(CH_3)_2$ | $-CO-CO-OC_2H_5$ | $n_D^{21}=1.5510$ |

The following compounds of formula I can also be prepared in accordance with the process described in Example 1:

| Compound No. | R₁ | R₂ | R₃ | R₄ | R₅ | R₆ |
|---|---|---|---|---|---|---|
| 31 | $-CH_3$ | $-CH_3$ | H | $-CH_3$ | $-C(CH_3)_3$ | $-CO-CO-OC_2H_5$ |
| 32 | $-CH_3$ | $-CH_3$ | 4-O-C₆H₄- | $-CH_3$ | $-C(CH_3)_3$ | $-CO-CO-OC_2H_5$ |
| 33 | $-CH(CH_3)_2$ | $-CH(CH_3)_2$ | 4-O-C₆H₄- | $-CH_3$ | $-C(CH_3)_3$ | $-CO-CO-OCH_3$ |
| 34 | $-CH(CH_3)_2$ | $-CH(CH_3)_2$ | 4-O-C₆H₄- | $-CH_3$ | $-C(CH_3)_3$ | $-CO-CO-N(CH_2H_5)_2$ |
| 35 | $-CH(CH_3)_2$ | $-CH(CH_3)_2$ | 4-O-C₆H₄- | $-CH_3$ | $-C(CH_3)_3$ | $-CO-C_6H_5$ |
| 36 | $-CH(CH_3)_2$ | $-CH(CH_3)_2$ | 4-O-C₆H₄- | $-CH_3$ | $-C(CH_3)_3$ | $-CO-OC_2H_5$ |
| 37 | $-CH(CH_3)_2$ | $-CH(CH_3)_2$ | 4-O-C₆H₄- | $-CH_3$ | $-CH(CH_3)_2$ | $-SO_2-CH_3$ |
| 38 | $-CH(CH_3)_2$ | $-CH_3$ | 4-O-C₆H₄- | $-CH_3$ | $-CH(CH_3)_2$ | $-CO-CO-N(CH_3)_2$ |
| 39 | $-C_2H_5$ | $-CH(CH_3)_2$ | H | $-C_2H_5$ | $-C(CH_3)_3$ | $-CO-CH_3$ |
| 40 | $-C_2H_5$ | $-CH(CH_3)_2$ | H | $-n-C_3H_7$ | $-C(CH_3)_3$ | $-CO-CH_3$ |
| 41 | $-C_2H_5$ | $-CH(CH_3)_2$ | H | $-CH_2-CH=CH_2$ | $-C(CH_3)_3$ | $-CO-CH_3$ |
| 42 | $-C_2H_5$ | $-CH(CH_3)_2$ | H | $-CH_2-C\equiv CH$ | $-C(CH_3)_3$ | $-CO-CH_3$ |
| 43 | $-CH(CH_3)_2$ | H | H | $-CH_3$ | $-C(CH_3)_3$ | $-CO-CO-OC_2H_5$ |
| 44 | $-CH(CH_3)_3$ | $-CH(CH_3)_2$ | 4-O-C₆H₄- | $-CH_3$ | $-C(CH_3)_3$ | $-CO-C_6H_3F_2$ (2,4-difluorophenyl) |

EXAMPLE 2

Action against *Laodelphax striatellus* and *Nilaparvata lugens* (nymphs)

The test is carried out with growing plants. The procedure is that 4 rice plants (thickness of stem 8 mm) about 20 cm in height are planted into each of a number of pots (diameter 8 cm). The plants in each pot are sprayed on a rotary table with 100 ml of acetonic solutions of test compound at concentrations rising from 3 ppm to 400 ppm. After the spray coating has dried, each plant is populated with 20 nymphs of the test organisms in the third stage. To prevent the cicadas from escaping, a glass cylinder is slipped over each of the plants and sealed with a gauze top. The nymphs are kept for 10 days on the treated plant until the next development stage has been reached. Evaluation of percentage mortality is made 1, 4 and 8 days after treatment.

When used at the following concentrations, the compounds of the invention effect 80–100% mortality after 8 days against nymphs of *Nilaparvata lugens:*

| Compound | Concentration of active ingredient |
|---|---|
| 1 | 3 ppm |
| 2, 14 and 17 | 50 ppm |
| 18 | 100 ppm |
| 7 and 19 | 200 ppm |
| 15 | 400 ppm |

Good activity against *Laodelphax striatellus* can also be achieved with the compounds of formula I according to Example 1.

EXAMPLE 3

Ovicidal action against *Laodelphax striatellus* and *Nilaparvate lugens*

The test is carried out with growing plants. The procedure is that 4 rice plants (thickness of stem 8 mm) about 20 cm in height are planted into each of a number of pots (diameter 8 cm). The plants in each pot are sprayed on a rotary table with 100 ml of a solution of the test compound in acetone at a concentration of 400 ppm. After the spray coating has dried, each plant is populated with 3 adult females. To prevent the cicadas from escaping, a glass cylinder is slipped over each of the plants and sealed with a gauze top. The females are kept on the treated plants for 4 days for oviposition and then removed. The young cicadas hatch about 8 days after population of the plants and a count is then made. The percentage mortality is assessed by comparing the number of hatched larvae on the treated plants with the number of those on the untreated controls. In this test, the compounds of formula I according to Example 1 have a good ovicidal action.

EXAMPLE 4

Insecticidal contact action against *Aphis craccivora*

Before the start of the test, bean plants (Vicia faba) which have been reared in pots are each populated with about 200 lice of the species *Aphis craccivora*. The treated plants are then sprayed to drip point 24 hours later with an aqueous composition containing 50 and 200 ppm respectively of the test compound. Two plants are used for each compound at its given concentration and a mortality count is made 24 hours later.

80–100% kill is achieved with compound 6 at 50 ppom and with compound 17 at 200 ppm.

EXAMPLE 5

Action against *Lucilia sericata*

1 ml of an aqueous solution containing 0.5% of test compound is added at 50° C. to 9 ml of a culture medium. Then about 30 freshly hatched *Lucilia sericata* larvae are added to the culture medium after 1 hour, and the insecticidal action is determined after 48 and 96 hours by evaluating the mortality rate. In this test, compounds of the formula I according to Example 1 exhibited good activity against *Lucilia sericata*.

EXAMPLE 6

Action against *Aedes aegypti*

A concentration of 800 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the solution of the test compound. Mortality counts are made after 1, 2 and 5 days.

In this test, compounds of Example 1 exhibited good activity against *Aedes aegypti*.

EXAMPLE 7

Insecticidal action against feeding insects

Cotton plants about 25 cm high, in pots, are sprayed with aqueous emulsions which contain the test compound in concentrations of 50 and 400 ppm. After the spray coating has dried, the cotton plants are popolated with *Spodoptera littoralis* and *Heliothis virescens* larvae in the $L_3$-stage. The test is carried out at 24° C. and 60% relative humidity. The percentage mortality of the test insects is determined after 120 hours.

With compounds 1 and 3 mortality is 80–100% against Spodoptera larvae at 50 ppm and against Heliothis larvae at 400 ppm.

EXAMPLE 8

Action against spider mites

*Phaseolus vulgaris* (dwarf bean) are infected with an infested piece of leaf from a mass culture of *Tetranychus urticae* 12 hours before the test for acaricidal activity. The mobile stages which have migrated to the plants are sprayed with the emulsified test preparations (concentration: 400 ppm) from a chromatography atomiser such that the spray mixture does not run off.

After two to seven days the number of dead and living larvae, adults and eggs are evaluated under a stereoscopic microscope and the result is expressed in percent. During the test run the treated plants are kept in greenhouse compartments at 25° C.

The compounds of formula I are effective in this test against eggs, larvae and adults of *Tetranychus urticae*.

EXAMPLE 9

Action against ticks (a) *Rhipicephalus bursa:*

Five adult ticks or 50 tick larvae are counted into each of a number of test tubes and immersed for 1 to 2 minutes in 2 ml of an aqueous emulsion containing a concentration of 800 ppm of test compound. Each test tube is then sealed with a cotton wool plug and placed on its head to enable the cotton wool to absorb the active ingredient emulsion.

Evaluation of the action against adults was made after 2 weeks and of that against larvae after 2 days. Each test was repeated twice.

(b) *Boophilus microplus* (larvae)

Tests are carried out with 20 OP-sensitive and 20 OP-resistant larvae using an active ingredient concentration similar to that described in (a). (The resistance refers to the tolerance towards diazinone). The compounds of the formula I according to Example 1 were very effective in tests (a) and (b).

EXAMPLE 10

Ovicidal action against *Spodoptera littoralis*

Eggs of *Spodoptera littoralis* deposited on filter paper are cut out of the paper and immersed an 0.5% by weight in solution of each compound to be tested in a 1:1 mixture of acetone-water. The treated deposits are then removed from this mixture and kept in plastic dishes at 21° C. and 60% humidity. The hatching rate, i.e. the number of larvae which have developed from the treated eggs, is determined after 5 days.

Compounds of formula I according to Example 1 were very effective in thist test.

EXAMPLE 11

Ovicidal action against *Heliothis virescens* and *Leptinotarsa decemlineata*

Corresponding amounts of a wettable powder formulation containing 25% by weight of the test compound are mixed with sufficient water to produce an aqueous emulsion with an active ingredient concentration of 800 ppm. One day-old egg deposits of Heliothis on cellophane and of Leptinotarsa on potato leaves are immersed in these emulsions for 3 minutes and then collected by suction on round filters. The treated deposits are placed in petri dishes and kept in the dark. The hatching rate in comparison wih untreated controls is determined after 6 to 8 days. Evaluation is made by determining the minimum concentration necessary for 80-100% kill of the eggs.

Compounds of formula I according to Example 1 were very effective in this test.

EXAMPLE 12

Action against soil insects (*Diabrotica balteata*)

350 ml of soil (consisting of 95 vol.% of sand and 5 vol.% of peat) are mixed with 150 ml of each of a number of aqueous emulsion formulations which contain the test compound in increasing concentrations of 3 ppm to 200 ppm. Plastic beakers with a diameter of about 10 cm at the top are then partly filled with the treated soil. Ten $L_3$ larvae of *Diabrotica balteata* are put into each beaker, then 4 maize seedlings are planted and the beaker is filled up the soil. The beakers are sealed with plastic sheeting and kept at about 22° C. Ten days later the soil in the beakers is sieved and a mortality count of the remaining larvae is made.

In this test the compounds of the invention effected 80-100% mortality when used in the concentrations indicated below:

| Compound | Concentration of active ingredient |
| --- | --- |
| 1 | 3 ppm |
| 2, 18 and 19 | 12.5 ppm |
| 2, 4, 9, 10, 13, 14 and 17 | 50 ppm |
| 7 | 100 ppm |
| 8 and 15 | 200 ppm |

What is claimed is:

1. A compound of the formula

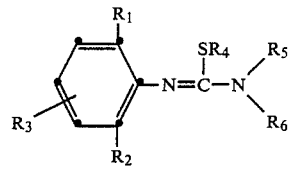

wherein
$R_1$ is C1-C5-alkyl,
$R_3$ is hydrogen, halogen, C1-C5-alkyl, phenoxy or phenoxy which is substituted by 1 or 2 identical or different members selected from the group consisting of halogen, C1-C5-alkyl or trifluoromethyl radicals,
$R_4$ is C1-C5-alkyl, allyl or propargyl,
$R_5$ is C1-C5-alkyl, C3-C6-cycloalkyl, allyl or propargyl, and (a)

$R_6$ is CO—R7, CO—CO—R8 or SO2—R7; and
$R_2$ is hydrogen or C1-C5-alkyl; or (b)

$R_6$ is CO—OR7; and
$R_2$ is C1-C5-alkyl;
wherein
$R_7$ is C1-C5-alkyl, phenyl or phenyl which is substituted by 1 or 2 halogen or methyl radicals, and
$R_8$ is C1-C10-alkoxy or di(C1-C5)-alkylamino.

2. A compound according to claim 1, wherein
$R_1$ is $C_1$-$C_4$alkyl,
$R_2$ is hydrogen or $C_1$-$C_5$alkyl,
$R_3$ is hydrogen, fluorine, chlorine, $C_1$-$C_3$alkyl, phenoxy or phenoxy which is substituted by 1 or 2 identical or different members selected from the group consisting of fluorine or chlorine atoms, methyl, ethyl or trifluoromethyl groups,
$R_4$ is $C_1$-$C_3$alkyl, allyl or propargyl,
$R_5$ is $C_2$-$C_5$alkyl, $C_3$-$C_6$cycloalkyl, allyl or propargyl, and
$R_6$ is a radical selected from —CO—$R_7$, —CO—CO—$R_8$, or —SO$_2$—$R_7$, wherein
$R_7$ is $C_1$-$C_4$alkyl, phenyl or phenyl which is substituted by 1 or 2 identical or different members selcted from the group consisting of fluorine or chlorine atoms or methyl groups, and
$R_8$ is $C_1$-$C_4$alkoxy or di($C_1$-$C_3$)alkylamino.

3. A compound according to claim 2, wherein
$R_1$ is $C_1$-$C_4$alkyl,
$R_2$ is $C_1$-$C_5$alkyl,
$R_3$ is hydrogen, fluorine, chlorine, methyl, phenoxy or phenoxy which is substituted by a member selected from the group consisting of fluorine, chlorine, methyl or trifluoromethyl,
$R_4$ is $C_1$-$C_3$alkyl, allyl or propargyl,
$R_5$ is $C_2$-$C_5$alkyl, cyclopropyl, cyclohexyl, allyl or propargyl, and
$R_6$ is a radical selected from —CO—$R_7$ or —CO—CO—$R_8$, wherein
$R_7$ is methyl, ethyl, phenyl or phenyl which is substituted by 1 or 2 fluorine or chlorine atoms, and
$R_8$ is methoxy, ethoxy, or dialkylamino in which alkyl is methyl or ethyl.

4. A compound according to claim 3, wherein
$R_1$ is $C_1$-$C_3$alkyl,
$R_2$ is $C_2$-$C_5$alkyl,
$R_3$ is hydrogen or 4-phenoxy, $R_4$ is $C_1$–$C_3$alkyl, allyl or propargyl,
$R_5$ is $C_2$–$C_5$alkyl,
$R_6$ is a radical selected from —CO—$R_7$ or —CO—CO—$R_8$, wherein
$R_7$ is methyl, ethyl, phenyl or difluorophenyl, and
$R_8$ is methoxy, ethoxy, dimethylamino or diethylamino.

5. A compound according to claim 4, wherein
$R_1$ is $C_1$–$C_3$alkyl,
$R_2$ is $C_2$–$C_4$alkyl,
$R_3$ is hydrogen or 4-phenoxy,
$R_4$ is methyl,
$R_5$ is $C_1$–$C_4$alkyl, and
$R_6$ is a —CO—$CH_3$ or —CO—CO—$OC_2H_5$ radical.

6. A compound according to claim 5, of the formula

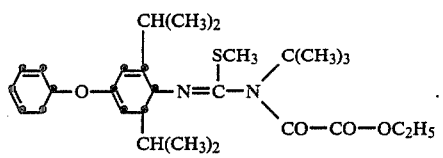

7. A compound according to claim 5, of the formula

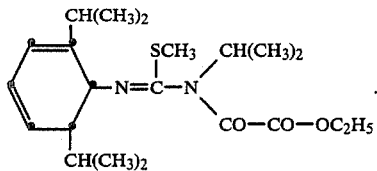

8. A compound according to claim 5, of the formula

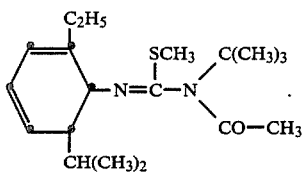

9. A composition for controlling plant destructive insects and representatives of the order Acarina, which composition comprises a pesticidally effective amount of a compound of claim 8, together with a carrier.

10. A composition for controlling plant destructive insects and representatives of the order Acarina, which composition comprises a pestically effective amount of a compound of claim 1, together with a carrier.

11. A compound according to claim 1 wherein R6 is —CO—OR7 and R2 is C1–C5-alkyl.

12. A compound according to claim 11 wherein R3 is 4-phenoxy or 4-phenoxy substituted by 1 or 2 halogen, C1–C5-alkyl or trifluoromethyl radicals.

13. A method for controlling plant destructive insects and representatives of the order Acarina, which method comprises applying at the locus of the plant an insecticidally effective amount of a compound of the formula

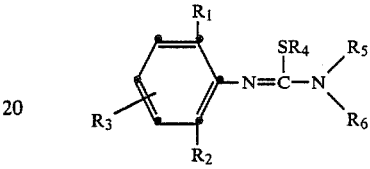

wherein
R1 is C1–C5-alkyl,
R2 is hydrogen or C1–C5-alkyl,
R3 is hydrogen, halogen, C1–C5-alkyl, phenoxy or phenoxy which is substituted by 1 or 2 identical or different members selected from the group consisting of halogen, C1–C5-alkyl or trifluoromethyl radicals,
R4 is C1–C5-alkyl, allyl or propargyl,
R5 is C1–C5-alkyl, C3–C6-cycloalkyl, allyl or propargyl, and
R6 is CO—R7, CO—OR7, CO—CO—R8 or SO2—R7; wherein
R7 is C1–C5-alkyl, phenyl or phenyl which is substituted by 1 or 2 halogen or methyl radicals, and
R8 is C1–C10-alkoxy or di(C1–C5)-alkylamino.

14. A method according to claim 13 wherein, in the formula of the compound applied, R6 is —CO—R7, —CO—CO—R8 or —SO2—R7.

15. A method according to claim 13 wherein, in the formula of the compound applied, R6 is —CO—OR7 and R2 is C1–C5-alkyl.

16. A compound according to claim 1 wherein R6 is —CO—CO—R8.

17. A compound according to claim 16 wherein R8 is alkoxy containing 1 to 10 carbon atoms.

* * * * *